(12) United States Patent
Mills et al.

(10) Patent No.: US 7,332,784 B2
(45) Date of Patent: *Feb. 19, 2008

(54) METHOD OF PROVIDING AN OPTOELECTRONIC ELEMENT WITH A NON-PROTRUDING LENS

(75) Inventors: Michael A. Mills, Mission Viejo, CA (US); James P. Coffin, IV, Trabuco Canyon, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/475,725

(22) Filed: Jun. 27, 2006

(65) Prior Publication Data

US 2007/0007612 A1 Jan. 11, 2007

Related U.S. Application Data

(60) Continuation of application No. 10/337,058, filed on Jan. 3, 2003, now Pat. No. 7,067,893, which is a division of application No. 09/038,494, filed on Mar. 10, 1998, now Pat. No. 6,525,386.

(51) Int. Cl.
*H01L 31/0203* (2006.01)
*H01L 31/0232* (2006.01)

(52) U.S. Cl. ............... 257/433; 257/432; 257/687; 257/787

(58) Field of Classification Search ........... 257/687, 257/787, 432–433; *H01L 31/0203, 31/0232*
See application file for complete search history.

(56) References Cited

U.S. PATENT DOCUMENTS

| | | | |
|---|---|---|---|
| 3,769,974 A | 11/1973 | Smart et al. | |
| 3,981,023 A | 9/1976 | King et al. | |
| 4,182,956 A | 1/1980 | Funk, Jr. et al. | |
| 4,267,559 A | 5/1981 | Johnson et al. | |
| 4,698,730 A | 10/1987 | Sakai et al. | |
| 4,703,219 A | 10/1987 | Mesquida | |
| 4,733,094 A | 3/1988 | Carpentier et al. | |
| 4,841,344 A | 6/1989 | Heinen | |
| 4,880,304 A | 11/1989 | Jaeb et al. | |
| 4,889,311 A | 12/1989 | Anglin | |

(Continued)

FOREIGN PATENT DOCUMENTS

JP 60-96424 5/1985

(Continued)

*Primary Examiner*—Theresa T Doan
(74) *Attorney, Agent, or Firm*—Knobbe Martens Olson & Bear LLP

(57) ABSTRACT

An optoelectronic component has a lens that is formed in the surface of an encapsulant surrounding a semiconductor diode element. With respect to emitters, the lens reduces internal reflection and reduces dispersion to increase overall efficiency. With respect to detectors, the lens focuses photons on the active area of the detector, increasing detector sensitivity, which allows a detector having a reduced size and reduced cost for a given application. The lens portion of the encapsulant is generally non-protruding from the surrounding portions of the encapsulant reducing contact surface pressure caused by the optoelectronic component. This non-protruding lens is particularly useful in pulse oximetry sensor applications. The lens is advantageously formed with a contoured-tip ejector pin incorporated into the encapsulant transfer mold, and the lens shape facilitates mold release.

19 Claims, 14 Drawing Sheets

U.S. PATENT DOCUMENTS

| | | | |
|---|---|---|---|
| 4,935,856 A | 6/1990 | Dragoon | |
| 4,946,242 A | 8/1990 | Tanno et al. | |
| 4,959,761 A | 9/1990 | Critelli et al. | |
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Polczynski | |
| 5,130,531 A | 7/1992 | Ito et al. | |
| 5,163,438 A | 11/1992 | Gordon et al. | |
| 5,249,576 A | 10/1993 | Goldberger et al. | |
| 5,296,715 A | 3/1994 | Kronberg | |
| 5,317,149 A * | 5/1994 | Uebbing et al. | ....... 250/231.14 |
| 5,337,744 A | 8/1994 | Branigan | |
| 5,347,605 A | 9/1994 | Isaksson | |
| D353,195 S | 12/1994 | Savage et al. | |
| D353,196 S | 12/1994 | Savage et al. | |
| 5,387,122 A | 2/1995 | Goldberger et al. | |
| 5,419,697 A | 5/1995 | Hirano et al. | |
| 5,431,170 A | 7/1995 | Mathews | |
| D361,840 S | 8/1995 | Savage et al. | |
| D362,063 S | 9/1995 | Savage et al. | |
| 5,452,717 A | 9/1995 | Branigan et al. | |
| 5,453,961 A | 9/1995 | Brazas | |
| RE35,069 E | 10/1995 | Hallenbeck et al. | |
| D363,120 S | 10/1995 | Savage et al. | |
| 5,482,036 A | 1/1996 | Diab et al. | |
| 5,485,317 A | 1/1996 | Perissinotto et al. | |
| 5,485,538 A | 1/1996 | Bowen et al. | |
| 5,487,124 A | 1/1996 | Bowen et al. | |
| 5,488,468 A | 1/1996 | Kawanishi et al. | |
| 5,490,505 A | 2/1996 | Diab et al. | |
| 5,494,043 A | 2/1996 | O'Sullivan et al. | |
| 5,506,445 A | 4/1996 | Rosenberg | |
| 5,516,727 A | 5/1996 | Broom | |
| 5,533,511 A | 7/1996 | Kaspari et al. | |
| 5,559,358 A | 9/1996 | Burns et al. | |
| 5,562,002 A | 10/1996 | Lalin | |
| 5,578,156 A | 11/1996 | Kamakura et al. | |
| 5,590,649 A | 1/1997 | Caro et al. | |
| 5,602,924 A | 2/1997 | Durand et al. | |
| 5,625,733 A | 4/1997 | Frigo et al. | |
| 5,631,987 A | 5/1997 | Lasky et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,678,544 A | 10/1997 | DeLonzor et al. | |
| 5,685,299 A | 11/1997 | Diab et al. | |
| D393,830 S | 4/1998 | Tobler et al. | |
| 5,743,261 A | 4/1998 | Mainiero et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,803,579 A | 9/1998 | Turnbull et al. | |
| 5,806,579 A | 9/1998 | Judkins | |
| 5,807,248 A | 9/1998 | Mills | |
| 5,810,734 A | 9/1998 | Caro et al. | |
| 5,823,950 A | 10/1998 | Diab et al. | |
| 5,830,131 A | 11/1998 | Caro et al. | |
| 5,833,618 A | 11/1998 | Caro et al. | |
| 5,844,722 A | 12/1998 | Stephens et al. | |
| 5,852,696 A | 12/1998 | Collins et al. | |
| 5,855,994 A | 1/1999 | Biebuyck et al. | |
| 5,860,919 A | 1/1999 | Kiani-Azarbayjany et al. | |
| 5,864,146 A | 1/1999 | Karellas | |
| 5,890,929 A | 4/1999 | Mills et al. | |
| 5,904,654 A | 5/1999 | Wohltmann et al. | |
| 5,913,819 A | 6/1999 | Taylor et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,970,749 A | 10/1999 | Bloom | |
| 5,985,214 A | 11/1999 | Stylli et al. | |
| 5,995,855 A | 11/1999 | Kiani et al. | |
| 5,997,343 A | 12/1999 | Mills et al. | |
| 6,002,952 A | 12/1999 | Diab et al. | |
| 6,011,986 A | 1/2000 | Diab et al. | |
| 6,027,452 A | 2/2000 | Flaherty et al. | |
| 6,036,642 A | 3/2000 | Diab et al. | |
| 6,045,509 A | 4/2000 | Caro et al. | |
| 6,067,462 A | 5/2000 | Diab et al. | |
| 6,081,735 A | 6/2000 | Diab et al. | |
| 6,088,607 A | 7/2000 | Diab et al. | |
| 6,110,522 A | 8/2000 | Lepper, Jr. et al. | |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,184,521 B1 | 2/2001 | Coffin, IV et al. | |
| 6,206,830 B1 | 3/2001 | Diab et al. | |
| 6,229,856 B1 | 5/2001 | Diab et al. | |
| 6,236,872 B1 | 5/2001 | Diab et al. | |
| 6,252,252 B1 | 6/2001 | Kunii et al. | |
| 6,256,523 B1 | 7/2001 | Diab et al. | |
| 6,263,222 B1 | 7/2001 | Diab et al. | |
| 6,274,924 B1 | 8/2001 | Carey et al. | |
| 6,278,522 B1 | 8/2001 | Lepper, Jr. et al. | |
| 6,280,213 B1 | 8/2001 | Tobler et al. | |
| 6,285,896 B1 | 9/2001 | Tobler et al. | |
| 6,321,100 B1 | 11/2001 | Parker | |
| 6,334,065 B1 | 12/2001 | Al-Ali et al. | |
| 6,343,224 B1 | 1/2002 | Parker | |
| 6,349,228 B1 | 2/2002 | Kiani et al. | |
| 6,360,114 B1 | 3/2002 | Diab et al. | |
| 6,371,921 B1 | 4/2002 | Caro et al. | |
| 6,374,129 B1 * | 4/2002 | Chin et al. | ................ 600/322 |
| 6,377,829 B1 | 4/2002 | Al-Ali | |
| 6,388,240 B2 | 5/2002 | Schulz et al. | |
| 6,397,091 B2 | 5/2002 | Diab et al. | |
| 6,430,525 B1 | 8/2002 | Weber et al. | |
| 6,463,311 B1 | 10/2002 | Diab | |
| 6,470,199 B1 | 10/2002 | Kopotic et al. | |
| 6,501,975 B2 | 12/2002 | Diab et al. | |
| 6,515,273 B2 | 2/2003 | Al-Ali | |
| 6,519,487 B1 | 2/2003 | Parker | |
| 6,525,386 B1 | 2/2003 | Mills et al. | |
| 6,526,300 B1 | 2/2003 | Kiani et al. | |
| 6,541,756 B2 | 4/2003 | Schulz et al. | |
| 6,542,764 B1 | 4/2003 | Al-Ali et al. | |
| 6,580,086 B1 | 6/2003 | Schulz et al. | |
| 6,584,336 B1 | 6/2003 | Ali et al. | |
| 6,595,316 B2 | 7/2003 | Cybulski et al. | |
| 6,597,933 B2 | 7/2003 | Kiani et al. | |
| 6,606,511 B1 | 8/2003 | Ali et al. | |
| 6,632,181 B2 | 10/2003 | Flaherty et al. | |
| 6,640,116 B2 | 10/2003 | Diab | |
| 6,643,530 B2 | 11/2003 | Diab et al. | |
| 6,650,917 B2 | 11/2003 | Diab et al. | |
| 6,654,624 B2 | 11/2003 | Diab et al. | |
| 6,658,276 B2 | 12/2003 | Kianl et al. | |
| 6,661,161 B1 | 12/2003 | Lanzo et al. | |
| 6,671,531 B2 | 12/2003 | Al-Ali et al. | |
| 6,678,543 B2 | 1/2004 | Diab et al. | |
| 6,684,090 B2 | 1/2004 | Ali et al. | |
| 6,684,091 B2 | 1/2004 | Parker | |
| 6,697,656 B1 | 2/2004 | Al-Ali | |
| 6,697,658 B2 | 2/2004 | Al-Ali | |
| RE38,476 E | 3/2004 | Diab et al. | |
| 6,699,194 B1 | 3/2004 | Diab et al. | |

| Patent No. | Date | Inventor |
|---|---|---|
| 6,714,804 B2 | 3/2004 | Al-Ali et al. |
| RE38,492 E | 4/2004 | Diab et al. |
| 6,721,585 B1 | 4/2004 | Parker |
| 6,725,075 B2 | 4/2004 | Al-Ali |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 * | 12/2004 | Mills et al. ............... 264/1.32 |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |

FOREIGN PATENT DOCUMENTS

| | | |
|---|---|---|
| JP | 360096424 A | 5/1985 |
| JP | 404025185 A | 1/1992 |
| JP | 404025185 A * | 1/1992 |
| JP | 6-310550 | 11/1994 |

* cited by examiner

METHOD OF PROVIDING AN OPTOELECTRONIC ELEMENT WITH A NON-PROTRUDING LENS

CLAIM OF PRIORITY

This application a continuation of U.S. patent application Ser. No. 10/337,058, filed Jan. 3, 2003 now U.S. Pat. No. 7,067,893, which is a divisional of U.S. patent application Ser. No. 09/038,494 filed Mar. 10, 1998 (now U.S. Pat. No. 6,525,386). The present application also incorporates the foregoing utility disclosures herein by reference.

BACKGROUND OF THE INVENTION

1. Field of the Invention

This invention relates to the field of optoelectronics, which includes light emitting components, such as light emitting diodes (LED) and laser diodes, and which also includes light detecting components, such as photodiodes, phototransistors, photodarlingtons and photovoltaic cells. Optoelectronics also includes various devices which incorporate optoelectronic components, such as displays, photosensors, optocouplers, and fiberoptic transmitters and receivers. In particular, this invention relates to lenses to increase the efficiency of optoelectronic emitters and the sensitivity of optoelectronic detectors.

2. Description of the Related Art

A prior art LED 100 is shown in FIG. 1 and consists of a semiconductor diode element 110 electrically connected to a leadframe 120 and surrounded by an encapsulating material 130. The diode element 110 is typically mounted to one lead 122 of the leadframe 120 and connected to a second lead 124 of the leadframe 120 by a wire bond 140. These two leads provide an electrical connection between an external current source and the anode and cathode of the diode element 110. The external current source supplies power to the diode device 100 that is converted to emitted light by the photoelectric effect, which occurs at the semiconductor junction within the diode element 110.

Internal inefficiencies within a semiconductor diode result in very low net efficiencies, which is the ratio of emitted light power to input power. Internal inefficiencies arise from a low ratio of minority carriers injected into the diode semiconductor junction to photons generated at the junction; photon loss due to internal reflection at the semiconductor/encapsulant interface; and absorption of photons within the semiconductor material. Because of these low net efficiencies, many LED applications require high input current, resulting in heat dissipation and device degradation problems in order to obtain sufficient light.

As illustrated in FIG. 1, the encapsulant 130 forms a flat light-transmitting surface 150. A flat surface is convenient in many applications where the LED is mounted to another surface that is also generally flat or in applications that otherwise cannot accommodate a protruding surface. The inefficiencies described above, however, are compounded by the configuration of the LED encapsulant/air interface. An encapsulant having a flat surface, such as in FIG. 1, allows photons transmitted by the diode element 110 to have considerable dispersion. A flat encapsulant surface also results in internal reflection at the encapsulant/air interface, further reducing photon transmission and increasing photon absorption within the encapsulant material.

FIG. 2 illustrates a prior art LED 200 having an encapsulant 230 that forms a spherical surface 250. A spherical or other curved surface gives a larger angle of incidence for photons emitted from the semiconductor diode element 210, reducing losses due to internal reflection. Further, this surface 250 acts as a lens to reduce the dispersion of generated photons. Unfortunately, a protrusion, such as this curved surface, is difficult to accommodate in many applications.

SUMMARY OF THE INVENTION

An optoelectronic device according to the present invention incorporates a lens that increases component performance. For example, the output of an LED utilizing the lens is increased by, in part, reducing internal reflection. Internal reflection results from the differing indices of refraction at the interface between the LED encapsulant and the surrounding air.

As shown in FIG. 3, when a light ray 310 passes from a media having a higher index of refraction 320 to a media having a lower index of refraction 330, the ray 310 is refracted away from the normal 340 to the surface 350. The angle, $\theta_1$, is customarily referred to as the angle of incidence 370 and the angle $\theta_2$ is customarily referred to as the angle of refraction 380. As the angle of incidence 370 is increased, the angle of refraction 380 increases at a greater rate, in accordance with Snell's Law:

$$\sin \theta_2 = (N_1/N_2) \sin \theta_1,$$

where ($N_1 > N_2$). When the angle of incidence 370 reaches a value such that $\sin \theta_1 = N_2/N_1$, then $\sin \theta_2 = 1.0$ and $\theta_2 = 90°$. At this point none of the light is transmitted through the surface 350, the ray 310 is totally reflected back into the denser medium 320, as is any ray which makes a greater angle to the normal 340. The angle at which total reflection occurs:

$$\theta_c = \arcsin N_2/N_1$$

is referred to as the critical angle. For an ordinary air-glass surface, where the index of refraction is 1.5, the critical angle is about 42°. For an index of 1.7, the critical angle is near 36°. For an index of 2.0, the critical angle is about 30°. For an index of 4.0, the critical angle is about 14.5°.

An optoelectronic device according to the present invention has an encapsulant that functions as a lens. For emitter applications, the lens reduces internal reflection and dispersion without having a protruding curved surface. Thus, LEDs utilizing the present invention have an improved efficiency compared with prior art flat-surfaced LEDs and similar devices, without the physical interface difficulties of the prior art curved-surface LEDs and similar devices. For detector applications, the lens focuses photons on the active area of the detector, increasing detector sensitivity. This increased detector sensitivity allows a detector having a reduced size, hence a reduced cost, to be used for a given application.

A particularly advantageous application of an optoelectronic device with a non-protruding lens is in pulse oximetry, and in particular, as an emitter in pulse oximetry probes. Pulse oximetry is the noninvasive measurement of the oxygen saturation level of arterial blood. Early detection of low blood oxygen saturation is critical because an insufficient supply of oxygen can result in brain damage and death in a matter of minutes. The use of pulse oximetry in operating rooms and critical care settings is widely accepted.

A pulse oximetry probe is a sensor having a photodiode which detects light projected through a capillary bed by, typically, red and infrared LED emitters. The probe is attached to a finger, for example, and connected to an instrument that measures oxygen saturation by computing the differential absorption of these two light wavelengths after transmission through the finger. The pulse oximetry instrument alternately activates the LED emitters then reads voltages indicating the resulting intensities detected at the photodiode. A ratio of detected intensities is calculated, and an arterial oxygen saturation value is empirically determined based on the ratio obtained:

$$I_{rd}/I_{ir} = \text{Ratio} \Rightarrow \% \ O_2 \ \text{Saturation}$$

Typically, a look up table or the like correlates the Ratio to saturation. The use of conventional LEDs within pulse oximetry probes has a number of drawbacks. Pulse oximetry performance is limited by signal-to-noise ratio which, in turn, is improved by high light output emitters. LEDs without lenses, such as illustrated in FIG. 1, are not optimized to transmit the maximum amount of light into the skin. LEDs with protruding lenses, such as illustrated in FIG. 2, create increased pressure on the skin, resulting in perfusion necrosis, i.e. a reduction of arterial blood flow, which is the medium to be measured. A solution to this problem in accordance with the present invention is an LED incorporating a non-protruding lens.

One aspect of the present invention is an optoelectronic device that comprises an encapsulant having a surface, a lens portion of the surface, and a filler portion having a generally planar surface. The filler portion is disposed around the lens, and the lens does not extend substantially beyond the plane of the generally planar surface. The optoelectronic device also comprises an optoelectronic element embedded in the encapsulant and operable at at least one wavelength of light. The lens being configured to transmit or receive the at least one wavelength.

Another aspect of the present invention is a mold tool for an optoelectronic device that comprises a first mold piece having a surface that defines a first cavity and an aperture within the first cavity. The mold tool also comprises a second mold piece having a surface which defines a second cavity. The first cavity and second cavity cooperate to form a molding compound into a predetermined shape. The mold tool further comprises an ejector pin having a contoured tip. The pin is movably located within the aperture between a first position retracted within the cavity and a second position extended from the aperture. In the first position, the tip constitutes an integral portion of the first cavity. In the second position, the ejector pin facilitates removal of the compound from the first cavity. The ejector pin tip at least partially defines the predetermined shape.

Another aspect of the present invention is an optoelectronic method comprising the steps of providing a generally planar surface at a predefined distance from an optoelectronic element, defining a light transmissive region of that surface within the critical angle of the optoelectronic element, and contouring the surface within the transmissive region without exceeding the predefined distance. These steps create a non-protruding lens for the optoelectronic element. In one embodiment, the transmissive region has a circular cross-section. The optoelectronic method can comprise the further step of shaping a surrounding region adjacent said transmissive region.

Yet another aspect of the present invention is an optoelectronic device comprising an encapsulant means for embedding an optoelectronic element and a lens means for conveying light between the optoelectronic element and a media surrounding the encapsulant means. In one embodiment, the optoelectronic device further comprises a flat surface means for providing a low-pressure contact surface for the lens means. In that embodiment, the optoelectronic device can further comprise an arcuate surface means for avoiding total internal reflection of light from the flat surface means. In another embodiment, the optoelectronic device further comprises a surrounding surface means for providing a contact surface for the encapsulant from which the lens means does not protrude.

BRIEF DESCRIPTION OF THE DRAWINGS

The present invention is described in detail below in connection with the following drawing figures in which.

DETAILED DESCRIPTION OF THE PREFERRED EMBODIMENTS

Figure 1:
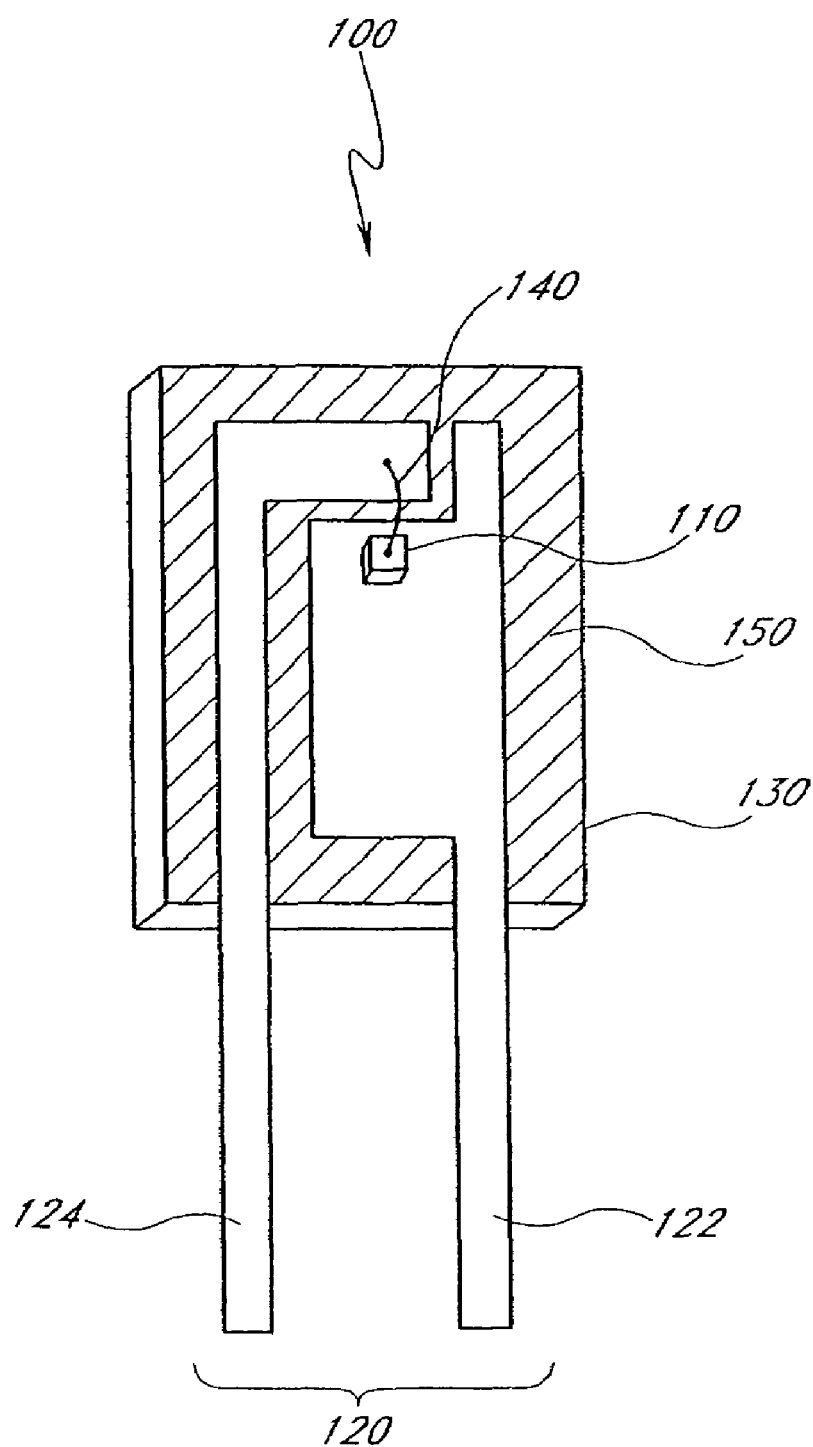
FIG. 1 is a cross-section view of a prior art LED having an encapsulant with a flat light-transmitting surface.
Figure 2:
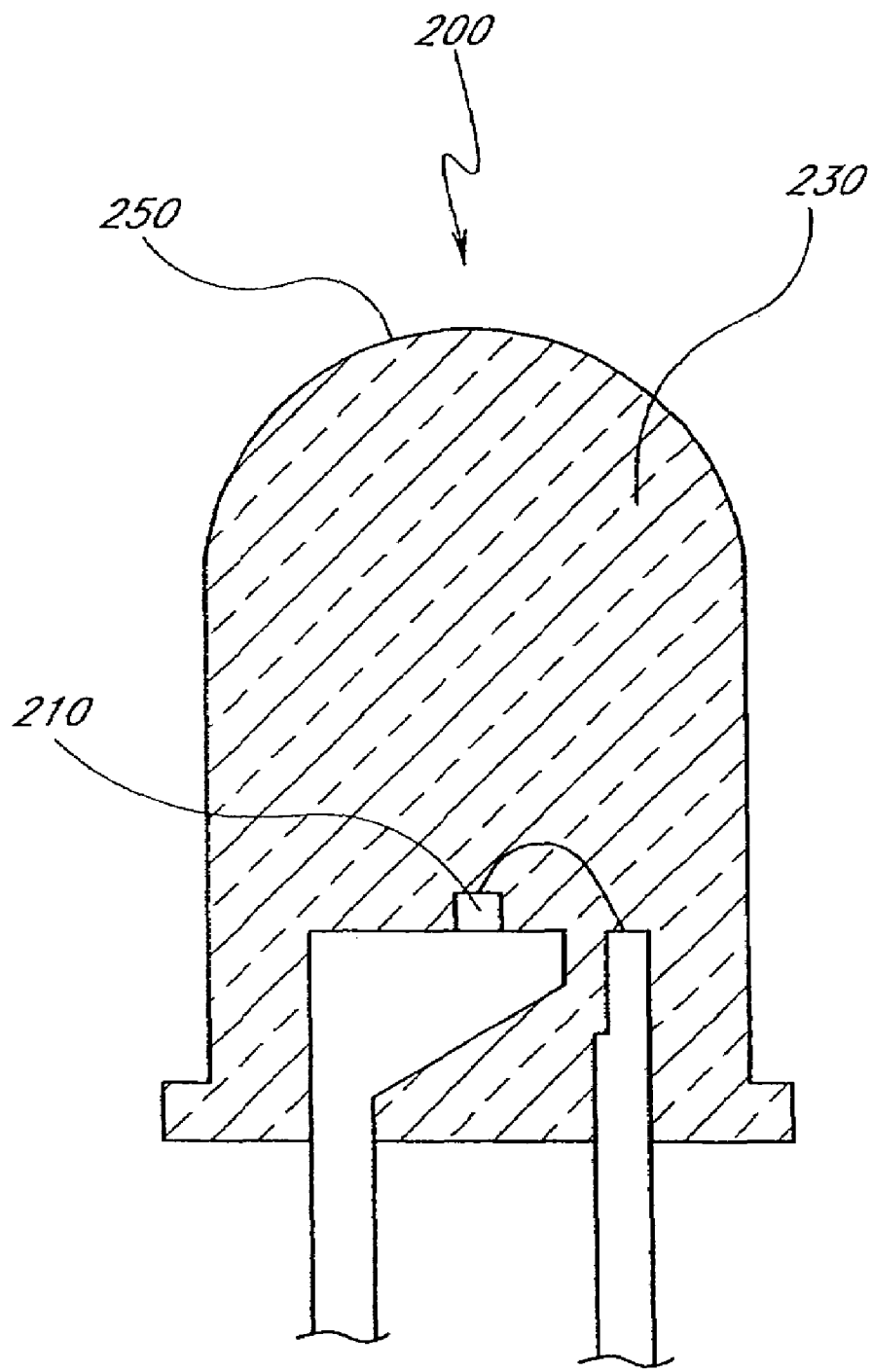
FIG. 2 is a cross-section view of a prior art LED incorporating a protruding, spherical light-transmitting surface.
Figure 3:
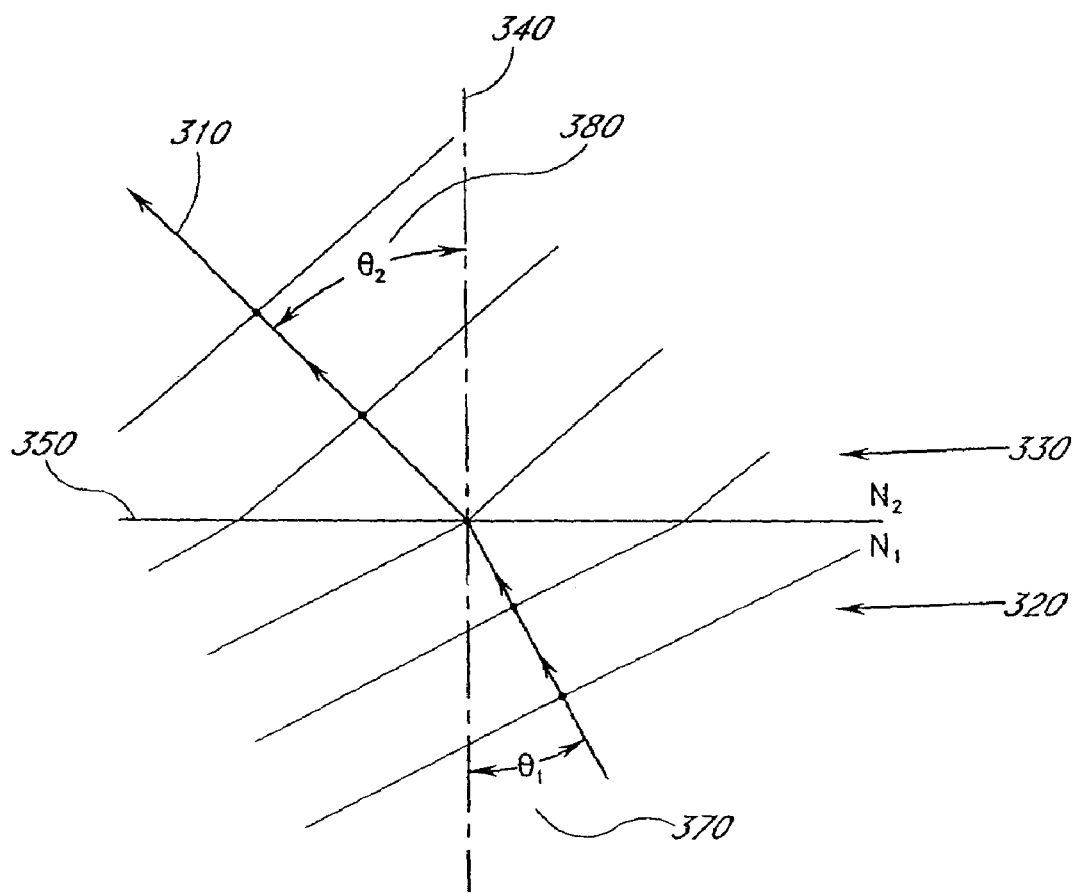
FIG. 3 generally illustrates light refraction at a surface between two media having different indices of refraction.
Figure 4:
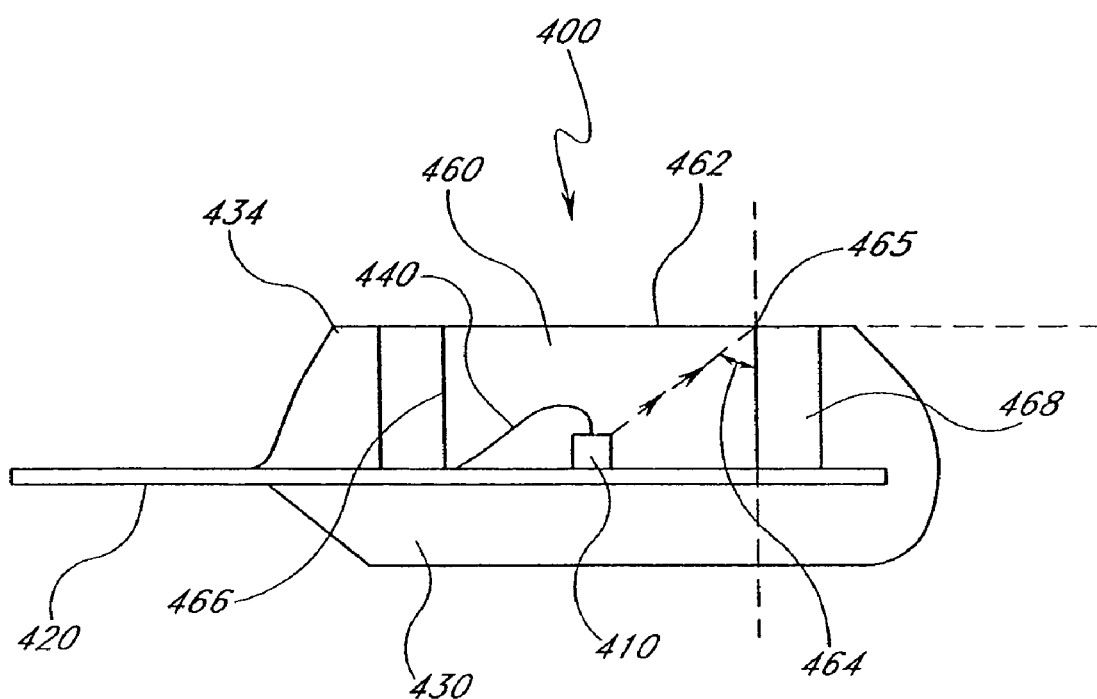
FIG. 4 is a cross-section view of an LED incorporating a single emitter and a flat-surfaced, vertical-side lens according to the present invention.

FIG. 4 illustrates an embodiment of an LED having a non-protruding or minimally protruding lens according to the present invention. The LED 400 consists of at least one semiconductor diode element 410, which is mounted to one lead of a leadframe 420 and connected to another lead of a leadframe 420 with a bond wire 440. The diode element 410, bond wire 440 and portions of the leadframe 420 are surrounded by an encapsulant 430. A lens 460 is molded into a portion of the encapsulant 430. The lens 460 has a generally flat, surface portion 462 that is at or below the plane of the surrounding surface portions 434 of the encapsulant 430. The lens extends radially from the diode element 410 out to the critical angle 464, at which point total internal reflection of photons emitted from the diode element would occur. Past the critical angle 464, the lens 460 has a steep side surface portion 466, which extends below the surface of the surrounding filler portion 434 of the encapsulant 430 to prevent internal reflection. A trough 468 is located between the flat surface portion 462 of the lens 460 and the surface of the surrounding filler portion 434 of the encapsulant 430. Due to refraction, light rays exiting the side surface portion 466 are bent towards the lens 460, reducing dispersion as compared to the prior art LED of FIG. 1.

Manufacturability considerations may limit the lens embodiment described above. If the lens side surface portion 466 is too steep, the LED may be difficult to release from the encapsulant mold. Further, the depth of the trough 468 may restrict the flow of encapsulant during the molding process and may also interfere with the bond wire 440. Optical considerations also may constrain this embodiment. The sharp transition 465 between the flat surface portion 462 and side surface portion 466 of the lens 460 results in an abrupt directional change of light rays exiting the lens 460 on either side of this transition 465, which may be problematic in some applications.

Figure 5A:
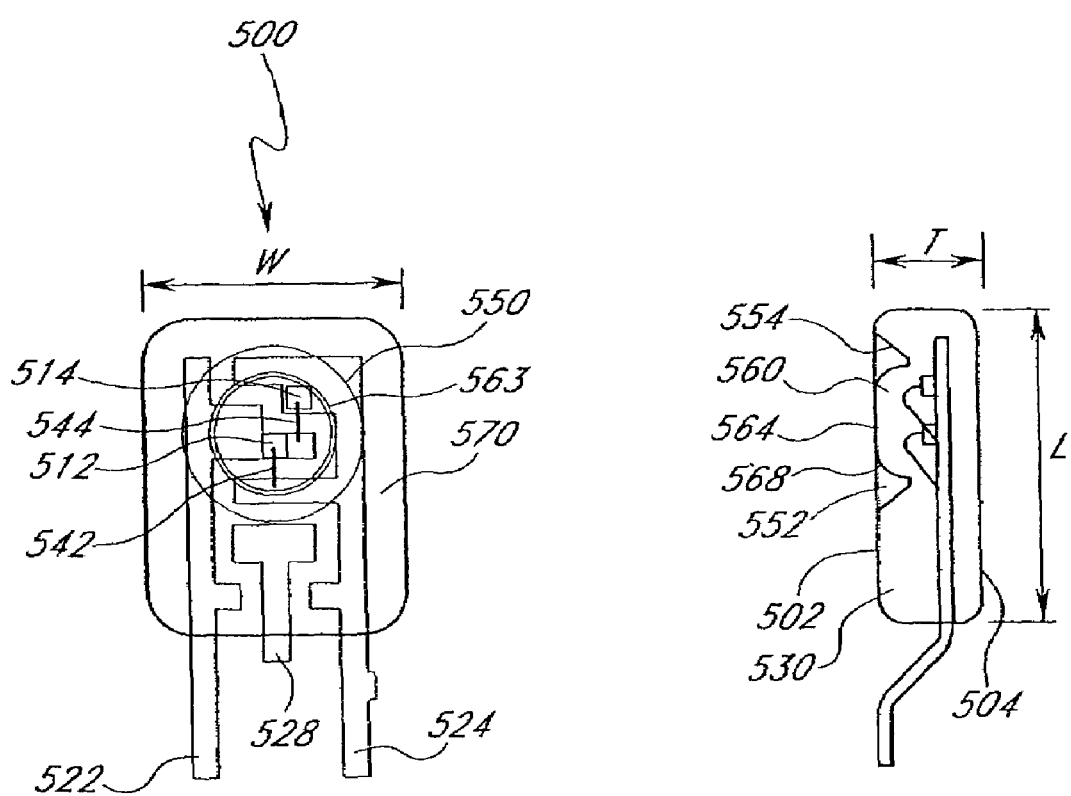
FIG. 5A is a plan view of an LED incorporating dual-emitters and a flat-element, non-protruding lens.

FIG. 5A illustrates an embodiment of a non-protruding lens LED for pulse oximetry applications. Pulse oximetry requires transmission of two wavelengths. Thus, this LED 500 utilizes dual semiconductor diode elements, a "red emitter" 512 producing wavelengths in the red portion of the spectrum and an "IR emitter" 514 producing infrared wavelengths. One type of red emitter is an AlGaAs chip available from, among others, Opto Tech Corporation, Hsinchu Science-Based Industrial Park, Taiwan, R.O.C., part number ED-014-UR/3. This part has a peak emission at 660±3 nm and a radiant power of 1.3 mW minimum. One type of IR emitter is a GaAs chip available from, among others, Infratech Corporation, 10440 Miller Road, Dallas, Tex., part number INF905N13H. This part has a peak emission at 905±10 nm and a radiant power of 1.8 mW typical.

The cathode side of the red emitter 512 is mounted to a first lead 522 and the cathode side of the IR emitter is mounted to a second lead 524. A third lead 528 is unused. A first bond wire 542 connects the anode side of the red emitter 512 to the second lead 524. A second bond wire 544 connects the anode side of the IR emitter 514 to the first lead 522. With this configuration, the red emitter 512 and IR emitter 514 are electrically connected in parallel and "back-to-back," i.e. cathode to anode. In this manner, the red emitter 512 and IR emitter 514 are activated one at a time by alternating the polarity of a voltage applied between the first lead 522 and second lead 524.

The semiconductor diode elements 512, 514, the leads 522, 524, 528 and associated bond wires 542, 544 are all encapsulated after the mounting and bonding process. Encapsulation is accomplished with a transfer mold process as described in detail below. The encapsulant 530 is molded into a standard-sized planar package having a length, L, of 220 mils, a width, W, of 170 mils and a thickness, T, of 70 mils. This forms a light transmitting side 502 and a backside 504 for the LED 500. One available encapsulant is HYSOL® MG18, which is from The Dexter Corporation, Electronic Materials Division, Industry, Calif. The index of refraction, $I_R$, for MG18 is 1.52. Thus, the critical angle, $\theta_c$, is arcsin(1/1.52)=41.1°. Another available encapsulant is NT-300H, which is from Nitto Denko America, Inc., 55 Nicholson Lane, San Jose, Calif. The index of refraction and critical angle for NT-300H is $I_R$=1.564 and $\theta_c$=39.7°

A lens is advantageously formed in the encapsulant during the molding process, as further described below. The light transmitting side 502 of the encapsulant 530 contains a contoured region 550 and a flat, filler region 570. The contoured region 550 is a shaped-surface within a circular cross-section 125 mils in diameter. The flat region 570 is a planar surface that surrounds the contoured region 550. Within the contoured region 550 are a lens 560 and a trough 552 having a sidewall 554. The lens 560 has a circular cross-section 563, a flat surface element 564, and an arcuate surface element 568. The flat surface element 564 is a substantially flat, circular portion of the lens 560 having a 30-mil diameter in one embodiment. The arcuate surface element 568 is a curved portion of the lens 560 having a 25-mil radius extending from the edge of the flat surface element 564 to the beginning of the trough 552 in one embodiment. The trough 552 has a depth of 22 mils and a bottom width of 4.2 mils in one embodiment. The sidewall 554 is constructed at an angle of 50° with respect to the flat region 570. With the lens configuration described above, the flat surface element 564 of the lens 560 is in the same plane as the flat region 570 surrounding the lens. This creates a non-protruding lens surface, which avoids pressure necrosis when the emitter with a lens in accordance with the present invention is used is a sensor.

Figure 5B:
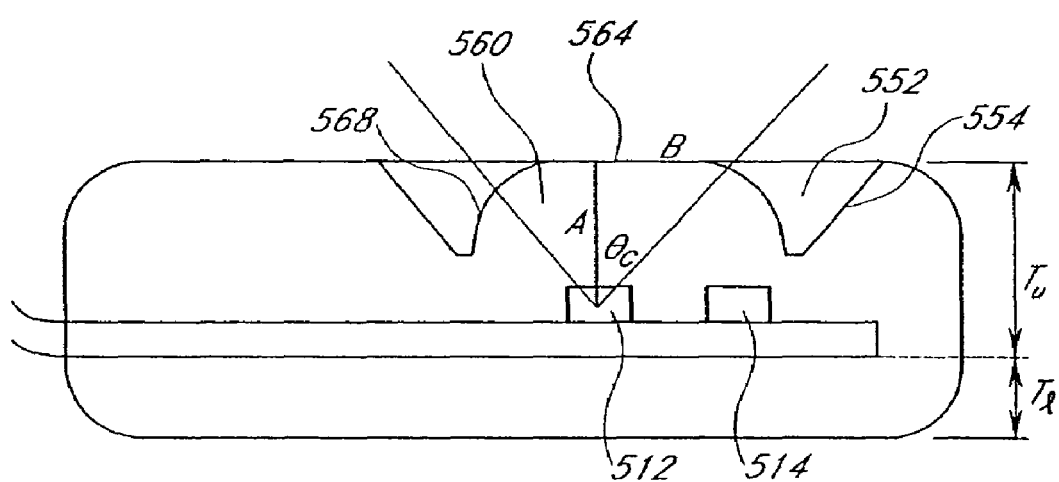
FIG. 5B is an enlarged view of a portion of FIG. 5A illustrating the critical angle.

As depicted in FIG. 5B, if the center of an emitter 512 is assumed to be a point source, the maximum distance, B, along the flat surface element before total internal reflection of light occurs is calculated as follows:

A=the distance to the lens surface

=thickness of encapsulant top-half–lead thickness–½ emitter thickness=(50–10–4)=36 mil $B/A$=tan $(\pi \cdot \theta_c/180°)$=0.83, for $\theta_c$=39.7°, therefore B=0.83·36≈30 mil Thus, the entirety of the flat surface element 564, which has a diameter of 30 mil, is within the critical angle of light rays from either the red emitter 512 or the IR emitter 514, as illustrated in FIG. 5B and by the calculations above.

The red emitter 512 is advantageously mounted only slightly offset with respect to the center of the lens 560. Although there is no total internal reflection of light from either emitter 512, 514 at any portion of the flat surface element 564, internal reflection increases as the incident angle approaches the critical angle. The red emitter 512 has a lower efficiency as compared to the IR emitter 514, as apparent from the 1.3 mW versus 1.8 mW radiant power, respectively, for the parts described above. The placement of the red emitter 512 near the lens center minimizes losses from internal reflection in the red spectrum to somewhat compensate for the red emitter's lower efficiency. This placement, however, is somewhat at the expense of the IR emitter 514, which has a higher efficiency and is, accordingly, mounted near the periphery of the lens 560 due to the space constraints imposed by the red emitter 512 placement and the configuration of the leads 522, 524 and bond wires 542, 544. At its location, the IR emitter 514 may incur significant internal reflection at portions of the lens 560 and uncalculated optical effects due to the proximity of the trough 552 and the trough sidewall 554.

The embodiment illustrated in FIGS. 5A-B overcomes the limitations of the non-protruding LED lens described with respect to FIG. 4. The trough 552 is shallow enough to allow encapsulant flow and to avoid bond wires. The sidewall 554 is angled to allow easy release of the part from the molding tool. The arcuate portion 568 provides a smooth transition between the flat surface portion 564 and the trough 552 to reduce corner effects.

Figure 6:
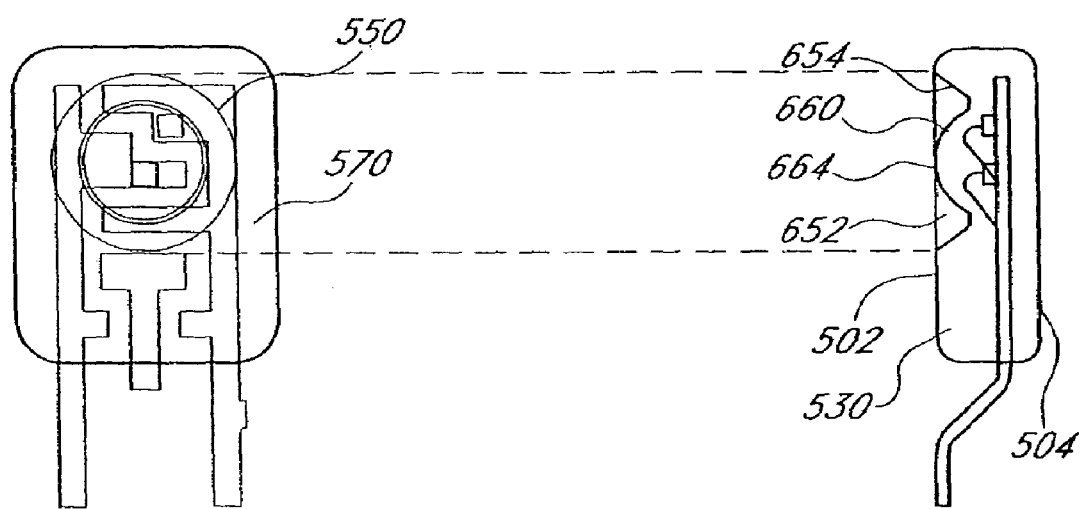
FIG. 6 is a plan view of another LED incorporating dual-emitters and a spherical-element, non-protruding LED lens.

FIG. 6 illustrates another preferred embodiment of the LED that incorporates a non-protruding spherical lens. As in the embodiment described with respect to FIGS. 5A-B, the light transmitting side 502 of the encapsulant 530 contains a contoured region 550 and a flat, filler region 570. The contoured region 550 and flat region 570 are as described above. Within the contoured region 550 are a lens 660 and a trough 652 having a sidewall 654. The lens 660 has a spherical surface element 664 having a curved surface with a radius of 50 mils. In this configuration, the trough 652 has a depth of 25 mils and a bottom width of 2.7 mils. The sidewall 654 is constructed at an angle of 56° 35' with respect to the flat region 570. With the lens configuration described above, the apex portion of the spherical surface element 664 is in the same plane as the flat region 570 surrounding the lens. As with the lens described with respect to FIGS. 5A-B, this creates a non-protruding lens surface, which avoids pressure necrosis. One of ordinary skill in the art will recognize that other lens shapes are also feasible within the scope of the current invention, such as a lens with a parabolic surface element.

Figure 7A:
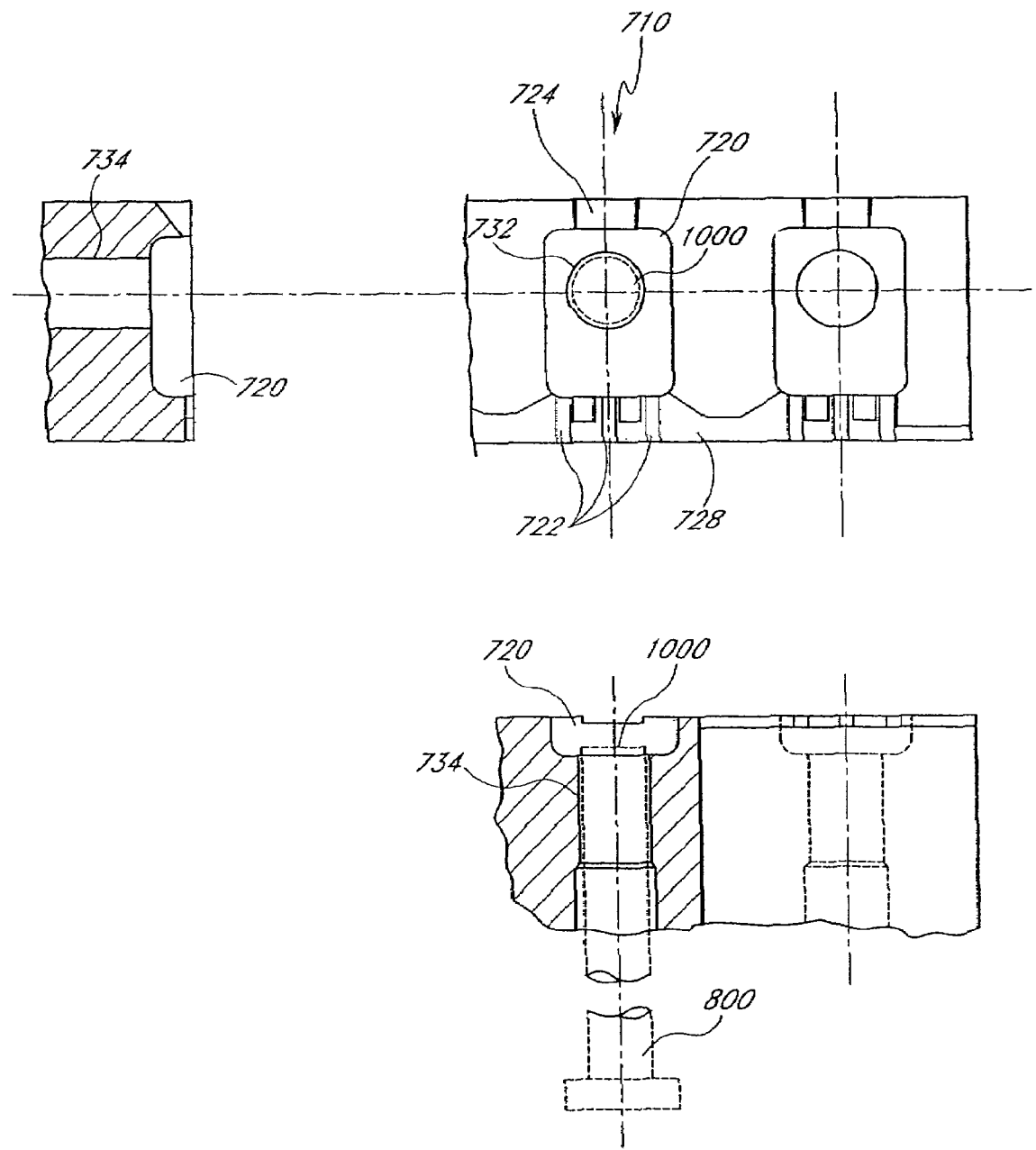
FIG. 7A is a plan view of the lower cavity of a production mold tool for encapsulating an optoelectronic element.

FIG. 7A depicts top, front and side views of the lower cavity portion 710 of a production transfer mold for encapsulating an LED according to the present invention. An available mold has 200 cavities and is manufactured by Neu Dynamics Corp., 110 Steamwhistle Drive, Ivyland, Pa., part number 97-3239. As shown in FIG. 7A, the lower cavity portion 710 has a cavity 720 for each LED to be molded. Placed into this mold are leadframe strips each containing the components for multiple LEDs. Each cavity has portions 722 to accommodate the three leadframe leads allocated to each LED. Each cavity 720 also has a gate 724 through which encapsulant is injected during the molding process, which is described in detail below. A vent 728 allows excess encapsulant and air to be ejected from the cavity. The depth of each cavity 720 is 50 mils, which, with reference to FIG. 5B, corresponds to the thickness, $T_u$, of the encapsulant upper half.

Each cavity 720 in the lower cavity portion 710 of the mold tool contains an ejector pin 800. When the mold press is opened, these ejector pins 800 protrude into the cavities 720, separating the encapsulated leadframes from the mold tool and allowing removal of the encapsulated leadframes. Within each cavity 720 is an aperture 732 that accommodates the ejector pin tip 1000 as described below. The ejector pin 800 for each cavity is installed in a shaft 734 in the body of the lower cavity portion 710.

Figure 7B:
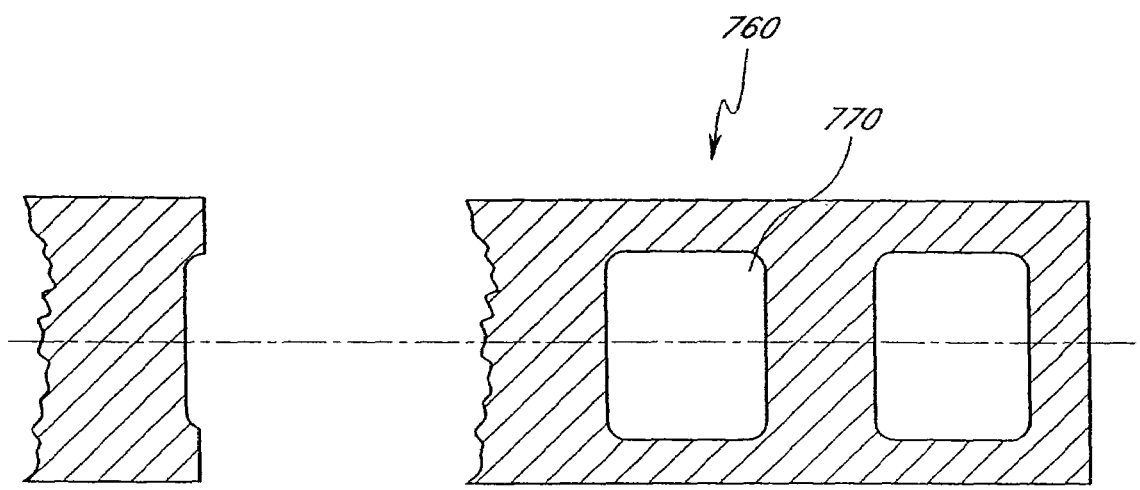
FIG. 7B is a plan view of the upper cavity of a production mold tool for encapsulating an optoelectronic element.

FIG. 7B depicts the upper cavity portion 760 of the production transfer mold corresponding to FIG. 7A. As shown in FIG. 7B, the upper cavity portion 760 has a cavity 770 for each LED to be molded. The depth of each cavity 770 is 20 mils, which, with reference to FIG. 5B, corresponds to the thickness, $T_1$, of the encapsulant lower half. The production mold, including the lower 710 and upper 760 cavity mold portions are mounted on lower and upper platens, respectively, of a standard production press. An available press is an 83-ton press manufactured by Fujiwa Seiki, model number TEP75-30, available from ESC International, Four Ivybrook Blvd., Ivyland, Pa.

A transfer molding process is utilized to encase the semiconductor diode elements, interconnecting gold bond wire and leadframe within a thermosetting epoxy resin, which is optically transmissive. Further conventional processing results in a completed LED device. Initially, the mold tool is brought to an operating temperature between 140-175° C. The mold tool is brought to an open position. One or more leadframes having multiple leads 522, 524, 528, mounted emitters 512, 514 and bond wires 542, 544 are loaded into a carriage so that the emitters 512, 514 will be face down in the lower mold cavities 720, which form the light emitting side 502 of the encapsulant 530. The leadframe carriage is then preheated to 325° F. and loaded into the mold tool. The mold press is closed, exerting maximum pressure on the mold tool. Mold compound pellets, which have been preheated for approximately 25 seconds to the consistency of a marshmallow are then loaded into a mold compound pot. A transfer ram injects the molten encapsulant into each cavity gate 724 at a pressure of between 500-1000 psi, and air and excess encapsulant are ejected through each cavity vent 728. The mold cycle time is between 2-5 minutes and nominally 3:00 minutes. After transfer molding, the clear molding resin is cured in an oven at 150° C.±10° C. for 2-4 hours.

Figure 7C:
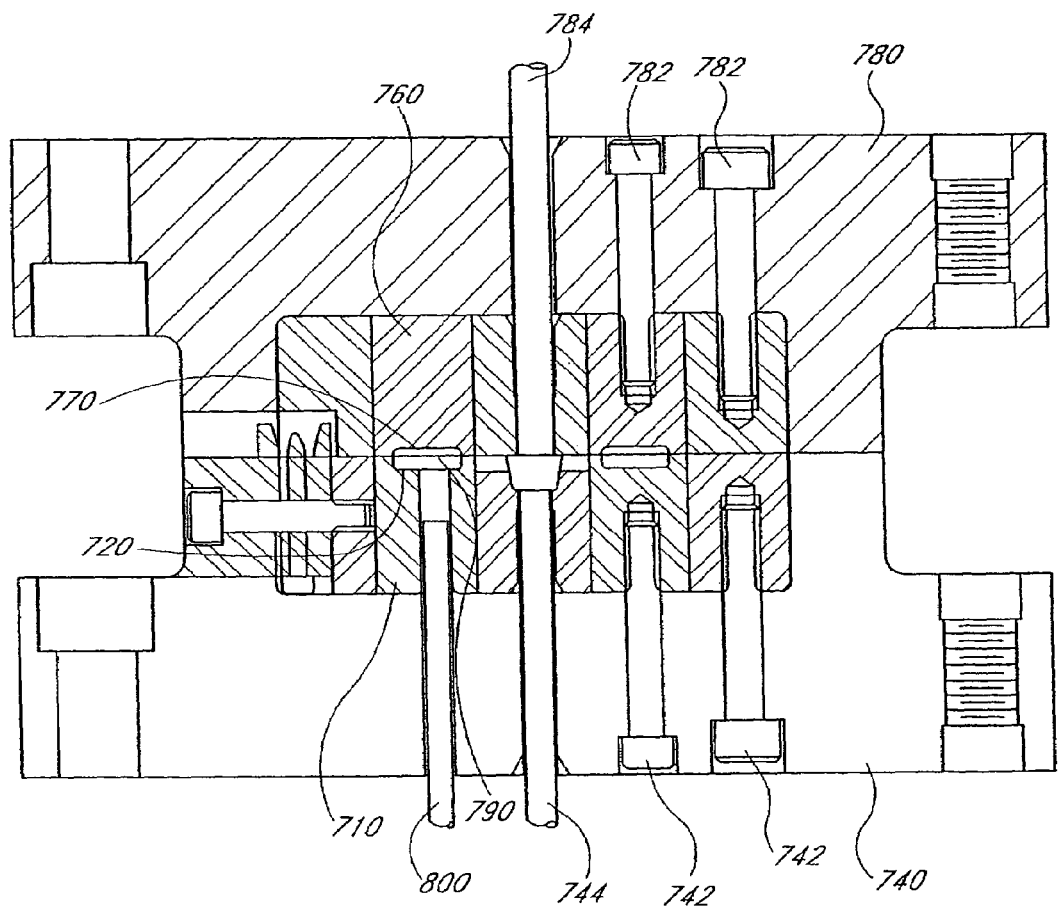
FIG. 7C is a cross section view of the upper cavity and the lower cavity of a production mold tool in a closed position.

FIG. 7C shows a side, cross-section view of the upper cavity portion 760 and the lower cavity portion 710 of the mold tool in the closed position. The upper cavity portion 760 is shown attached to the upper mold tool base 780 with bolts 782. The lower cavity portion 710 is shown attached to the lower mold tool base 740 with bolts 742. In this closed position, each upper cavity 770 and lower cavity 720 together form a whole cavity 790 that accepts and shapes mold compound to form the LED encapsulant. Also shown is a cavity ejector pin 800 that functions as described above for separating an encapsulated leadframe from the mold tool. In addition, there is a runner ejector pin 744 that functions similarly to the cavity ejector pin 800 to separate an encapsulated leadframe from the mold tool. A runner holddown pin 784 serves to position a leadframe within the mold tool.

Figure 8A:
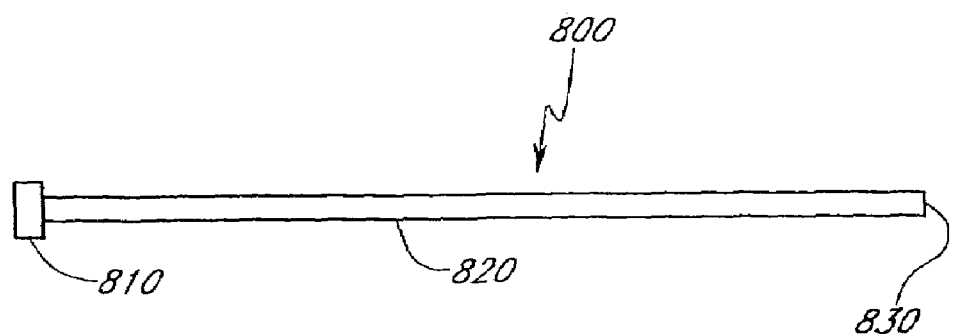
FIG. 8A is an illustration of a prior art ejector pin for a production mold tool.
Figure 8B:
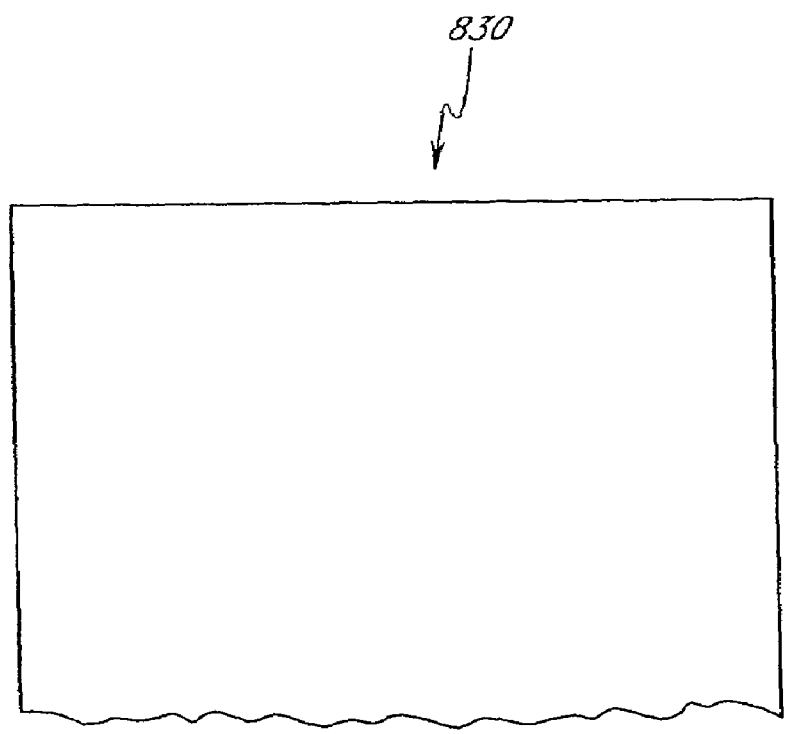
FIG. 8B is a cross-section view of a prior art ejector pin tip.
Figure 10A:
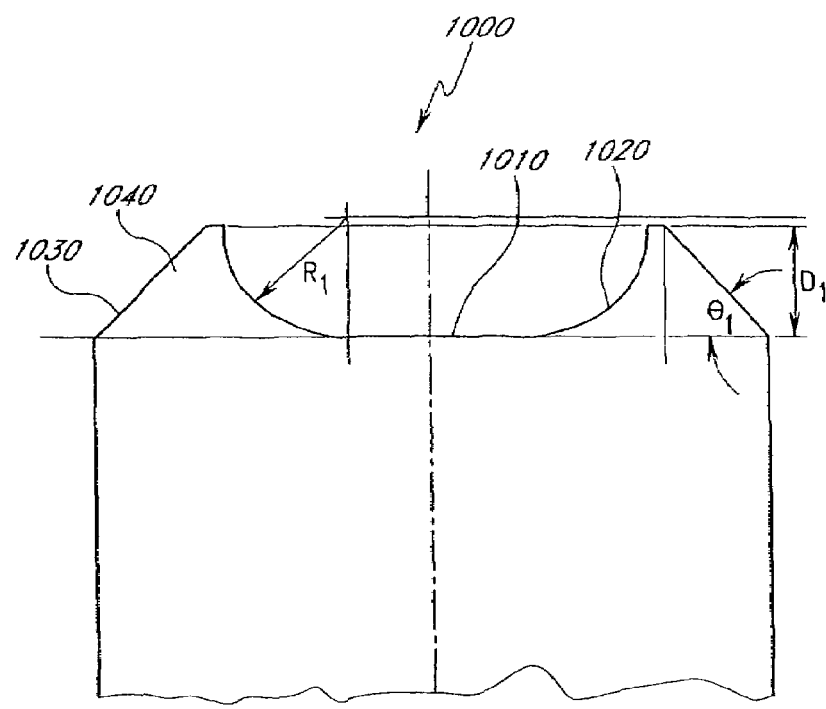
FIG. 10A is a cross-section view of an ejector pin tip for creating a non-protruding optoelectronic lens featuring a flat surface element.
Figure 10B:
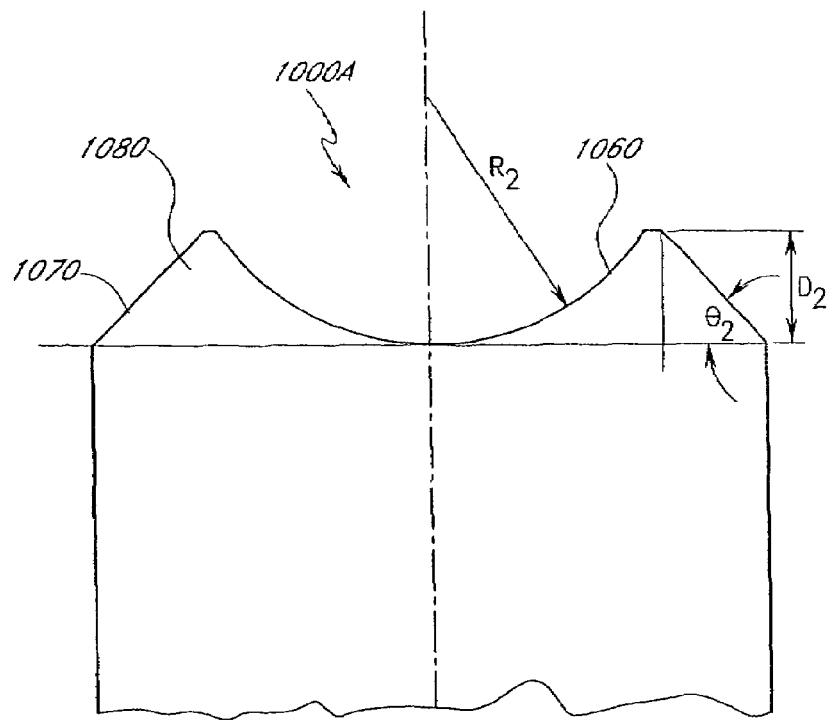
FIG. 10B is a cross-section view of an ejector pin tip for creating a non-protruding optoelectronic lens featuring a spherical surface element.

FIG. 8A illustrates a conventional ejector pin 800. The pin 800 has a base 810, a rod 820 and a tip 830. FIG. 8B illustrates the flat surface at the tip 830 of a prior art ejector pin 800. A pin 801 with a contoured tip 1000 according to the present invention, as described below with respect to FIGS. 10A-B, is installed in the shaft 734 of the lower cavity portion 710 described with reference to FIG. 7A. The rod 820 can freely slide within the shaft 734 such that the tip 1000 is flush with or protrudes into the cavity 720 through the aperture 732. A separate portion of the mold tool presses against the base 810 to actuate the ejector pin 800 when the press is opened or closed. With the prior art ejector pin 800, discontinuities between the pin tip 830 and the surrounding tool and the fact that the pin tip 830 is not exactly flush with the surrounding tool result in imperfections on the surface of the mold compound. This undesirable ejector pin mark typically has to be polished off or placed on a portion of the molded part where the mark has no effect. With respect to molding LED devices, the ejector pin mark can distort the optical properties of the LED encapsulant surface. As a result, in a typical LED molding process, ejector pins are placed on the backside or non-emitting surface of the LED.

Figure 9:
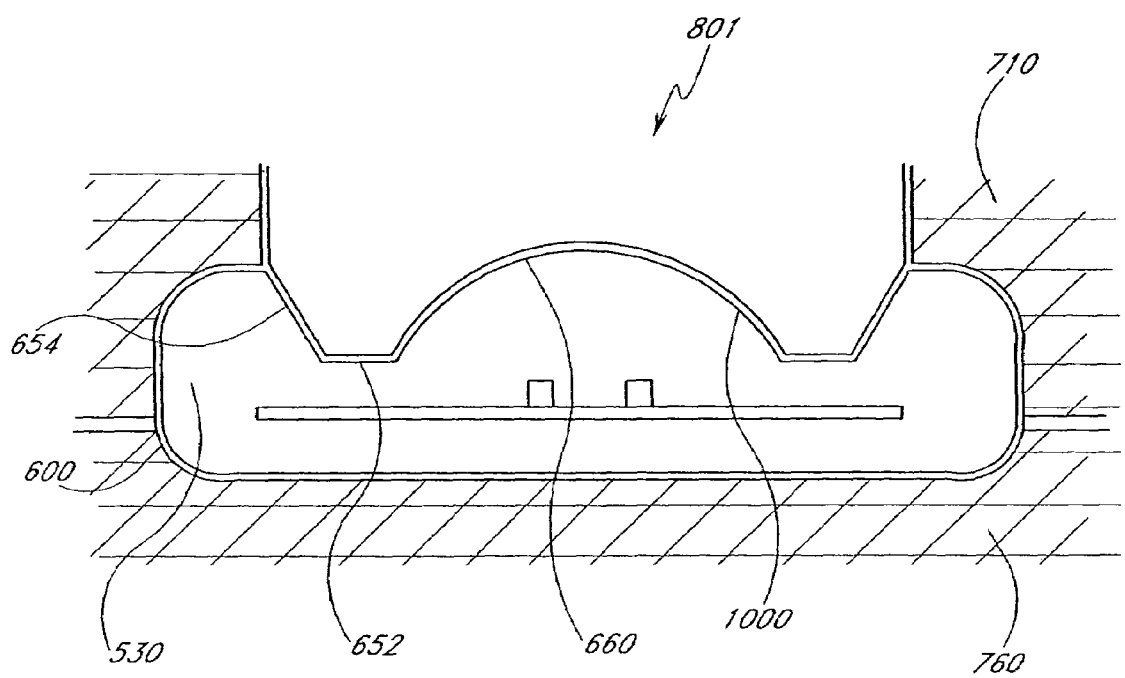
FIG. 9 is a cross-section view of a non-protruding optoelectronic lens being formed in a mold tool with a contoured ejector pin tip according to the present invention.

FIG. 9 illustrates a mold tool that advantageously utilizes the presence of the ejector pin in each mold cavity to shape the mold compound. This is in stark contrast to the prior art, which attempts to minimize the ejector pin effect. With respect to molding an LED, such as that shown in FIG. 6, the ejector pin 800 is located such that it contacts the light transmitting surface 502 of the LED 600, rather than the backside surface 504. The ejector pin 800 is located within a cavity 720 of the lower cavity portion 710 of the mold tool so that it becomes an integral part of the molding process. As illustrated in FIG. 9, the pin tip 1000 is contoured to form the lens 660, trough 652 and trough sidewall 654 of the LED 600.

The ejector pin 801 according to the present invention functions both to remove the molded parts from the tool and impart a contour to the surface of the LED. As shown in FIG. 9, in the mold tool closed position, the ejector pin 801 provides a shaped surface for molding a lens 660 into the encapsulant 530. In the mold tool open position, the ejector pin 801 serves the function of separating the encapsulated LED 600 from the mold tool 710 to facilitate removal.

FIG. 10A illustrates an embodiment of a contoured-tip ejector pin according to the present invention. The ejector pin tip 1000 is advantageously shaped to create an LED 500 having a non-protruding lens 560 with a flat surface element 564 corresponding to the illustration of FIG. 5A. The ejector pin tip 1000 of FIG. 10A has an optically ground and polished flat circular surface 1010 of 30 mil diameter which corresponds to the flat surface element 564 of the LED lens 560. The ejector pin tip 1000 also features a curved portion 1020 of 25 mil radius, $R_1$, blending into the flat surface 1010 which is similarly ground into the pin tip 1000 and which corresponds to the arcuate surface element 568 of the LED lens 560. The pin tip 1000 has a combination of a 50° angle, $\theta_1$, and a 0.023 inch height, $D_1$, taper 1030 ground and optically polished on the outer diameter of the pin tip 1000 which corresponds to the LED encapsulant sidewall 554. The tip area 1040 between the curved portion 1020 and taper 1030 corresponds to the LED encapsulant trough 552.

FIG. 10B illustrates another embodiment of a contoured-tip ejector pin according to the present invention. The ejector pin tip 1000A is advantageously shaped to create an LED 600 having a non-protruding lens 660 with a spherical surface element 664 corresponding to the illustration of FIG. 6. The ejector pin tip 1000A of FIG. 10B has an optically ground and polished spherical dome 1060 of 50-mil radius, $R_2$, which corresponds to the spherical surface element 664. The tip 1000A also has a 56°, 35' angle, $\theta_2$, and 0.025 inch height, $D_2$, taper 1070 ground and optically polished on the outer diameter of the pin tip 1000A which corresponds to the encapsulant sidewall 654. The tip area 1080 between the spherical dome 1060 and taper 1070 corresponds to the encapsulant trough 652. Neu Dynamics, Ivyland, Pa., is capable of manufacturing ejector pins with contoured tips such as shown in FIGS. 10A-B.

Figure 10C:
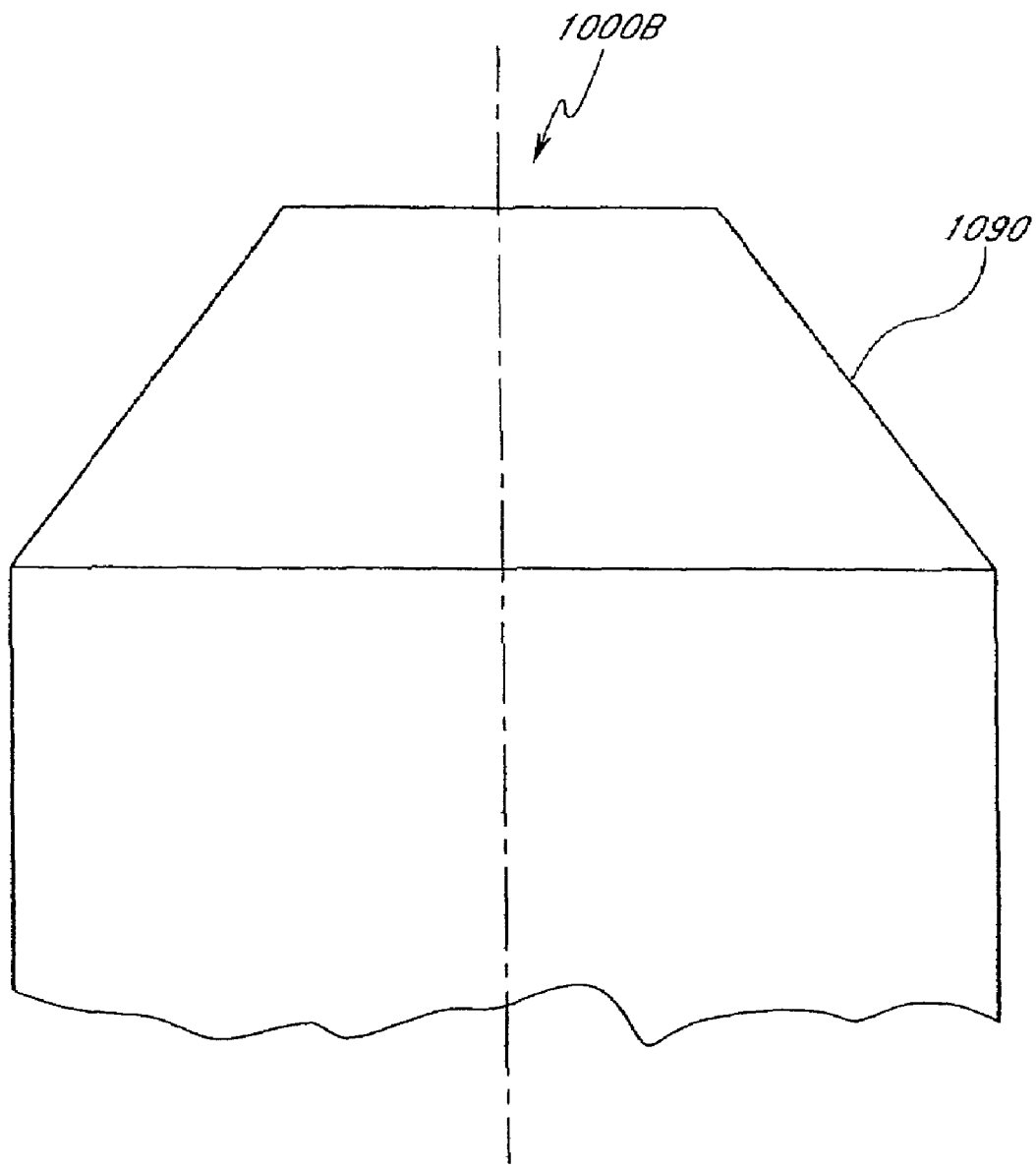
FIG. 10C is a cross-section view of an ejector pin tip for creating a detector cavity.

FIG. 10C illustrates yet another embodiment of a contoured-tip ejector pin according to the present invention. The ejector pin tip 1000B is advantageously shaped to create a generally cone-shaped chamber in the encapsulant to concentrate or "funnel" energy onto the surface of a detector element embedded in the encapsulant. This creates a one-piece detector device that functions similarly to a photodetector mounted within a separate chamber, as described in U.S. Pat. No. 5,638,818 and assigned to the assignee of the present invention. The tip 1000B features a taper 1090 that is ground and optically polished on the outer diameter of the pin tip 1000B and that corresponds to the chamber walls.

The non-protruding optoelectronic lens and associated contoured-tip ejector pins have been disclosed in detail in connection with the various embodiments of the present invention. These embodiments are disclosed by way of examples only and are not to limit the scope of the present invention, which is defined by the claims that follow. One of ordinary skill in the art will appreciate many variations and modifications within the scope of this invention. For example, although the current invention was described above mostly with respect to LED embodiments, the current invention also applies to non-protruding lenses for encapsulated photodiode detectors and to detector cavities.

What is claimed is:

1. A mold tool for an optoelectronic device comprising:
   a first mold piece having a surface that defines a first cavity and that defines an aperture within said first cavity;
   a second mold piece having a surface which defines a second cavity, said first cavity cooperating with said second cavity to at least partially form a molding compound into a predetermined shape; and
   an ejector pin movably located within said aperture to facilitate removal of said compound from said first cavity, wherein said predetermined shape comprising a generally flat surface and a generally contoured surface at least partially within and not extending above said flat surface, said contoured surface including a lens surrounded by a trough, at least a portion of said trough including a sidewall opposite said lens, said predetermined shape embedding at least one optoelectronic element.

2. The mold tool of claim 1, wherein said ejector pin includes a contoured tip movably located within said aperture to form an integral portion of said first cavity, wherein said predetermined shape is at least partially defined by said contoured tip.

3. The mold tool of claim 2, wherein said contoured tip forms a surface configured to shape said compound into said lens.

4. The mold tool of claim 2, wherein said contoured tip forms a surface configured to shape said compound into said trough.

5. The mold tool of claim 2, wherein said contoured tip forms a surface configured to shape said compound into said trough sidewall.

6. The mold tool of claim 1, wherein said lens comprises a generally flat circular surface ending with an arcuate surface at its periphery.

7. The mold tool of claim 1, wherein said lens comprises a generally spherical surface.

8. The mold tool of claim 1, wherein said lens comprises a generally parabolic surface.

9. A mold for an optoelectronic device comprising:
   a first mold section defining a first cavity; and
   a second mold section defining a second cavity, wherein the first and second mold sections cooperate to form an encapsulant into a desired shape embedding a plurality of leads and at least one optoelectronic device comprising one of an emitter or a detector of a noninvasive optical oximetry sensor, the shape of the encapsulate including a generally flat surface and a generally contoured surface at least partially within and not extending above said flat surface, said contoured surface including a lens surrounded by a trough, at least a portion of said trough including a sidewall opposite said lens.

10. The mold of claim 9, wherein said at least one optoelectronic device comprises a plurality of emitters.

11. The mold of claim 10, wherein said emitters comprises first and second emitters.

12. The mold of claim 11, wherein said first emitter includes a first efficiency, said second emitter includes a second efficiency higher than said first efficiency, and wherein said first emitter is more centered under said lens than said second emitter.

13. The mold of claim 9, wherein said first mold section comprises an ejector pin including a contoured tip forming an integral portion of said first cavity, wherein said shape is at least partially defined by said contoured tip.

14. The mold of claim 13, wherein said contoured tip forms a surface of said first cavity configured to shape said encapsulant into said lens.

15. The mold of claim 13, wherein said contoured tip forms a surface of said first cavity configured to shape said encapsulant into said trough.

16. The mold of claim 13, wherein said contoured tip forms a surface of said first cavity configured to shape said encapsulant into said trough sidewall.

17. The mold of claim 9, wherein said lens comprises a generally flat circular surface ending with an arcuate surface at its periphery.

18. The mold of claim 9, wherein said lens comprises a generally spherical surface.

19. The mold of claim 9, wherein said lens comprises a generally parabolic surface.

* * * * *